US006388133B1

(12) United States Patent
Chambers et al.

(10) Patent No.: US 6,388,133 B1
(45) Date of Patent: May 14, 2002

(54) FLUORINATION OF KETOAMIDES

(75) Inventors: Richard Dickinson Chambers; John Hutchinson, both of Durham; Julie Thomson, Preston, all of (GB)

(73) Assignee: F2 Chemicals Limited (GB)

( * ) Notice: Subject to any disclaimer, the term of this patent is extended or adjusted under 35 U.S.C. 154(b) by 0 days.

(21) Appl. No.: 09/230,970

(22) PCT Filed: Jul. 24, 1997

(86) PCT No.: PCT/GB97/02002

§ 371 Date: Dec. 9, 1999

§ 102(e) Date: Dec. 9, 1999

(87) PCT Pub. No.: WO98/05628

PCT Pub. Date: Feb. 12, 1998

(30) Foreign Application Priority Data

Aug. 1, 1996 (GB) .............................................. 9616226

(51) Int. Cl.[7] .............................................. C07C 233/05
(52) U.S. Cl. .................... 564/199; 564/200; 564/209
(58) Field of Search ................. 564/199, 200, 564/209

(56) References Cited

U.S. PATENT DOCUMENTS 5,049,698 A * 9/1991 Newland .................... 560/174
5,362,919 A * 11/1994 Costeloo et al. ............ 568/601
5,525,729 A * 6/1996 Cabrera et al. ................ 544/2
5,756,000 A * 5/1998 Hansen et al. .............. 252/307

FOREIGN PATENT DOCUMENTS

| EP | 0667332 A1 | 8/1995 | ........... C07C/45/63 |
| WO | WO 95/14646 | 6/1995 | |

OTHER PUBLICATIONS

Banks et al.; Efficient Electrophilic Fluorination of $_\beta$–Dicarbonyl Compounds with the Selectfluor Reagent F–TED–A–BF$_4$ (1–Chloromethyl–4–fluoro–1,4–diazoniabicyclo [2.2.2]octane, J. Chem. Soc., Chem. Commun., 343–344 (1994).
International Search Report, PCT/GB97/02002.
March; *Advanced Organic Chemistry*, 4th Edition, pp. 534, 587 (1992).

* cited by examiner

*Primary Examiner*—Shailendra Kumar
(74) *Attorney, Agent, or Firm*—Myers Bigel Sibley & Sajovec

(57) ABSTRACT

A process for the preparation of an N,N-disubstituted-2-fluoro-1,3-ketoamide having the formula RCO.CFR'CONR$_2$" comprises treating an N,N-disubstituted-1,3-ketoamide having the formula RCO.CHR'CONR$_2$" with elemental fluorine. The groups R, R' and R" are independently selected from alkyl, aryl, substituted aryl, cycloalkyl, and substituted cycloalkyl. The group R' may also be nitro or chlorine.

15 Claims, No Drawings

FLUORINATION OF KETOAMIDES

This application is a 371 of PCT/GB97/02002, filed Jul. 24, 1997.

This invention relates to the fluorination of ketoamides and in particular to the fluorination of N,N-disubstituted-β-ketoamides.

There is much interest in the preparation of fluorinated-1,3-dicarbonyl compounds since they are useful building blocks for the preparation of more complex molecules containing fluorine that are of potential value to both the pharmaceutical and agrochemical industries. For example, the replacement of the 2-hydrogen by fluorine in N,N-disubstituted-1,3-ketoamides affords fluorinated products that may be used in the preparation of potentially useful bio-active molecules. Hitherto, this transformation has been carried out by treating N,N-disubstituted-1,3-ketoamides with electrophilic fluorinating reagents such as 1-(chloromethyl)-4-fluoro-1,4-diazoniabicyclo-[2.2.2]octane.bi(tetrafluoroborate) sold under the Trade Mark SELECTFLUOR (R E Banks, N J Lawrence and A L Popplewell; J Chem Soc., Chem Commun., 1994, 343). However, such reagents are expensive, often unstable, difficult to handle and require fluorine for their preparation. There would seem to be advantage in carrying out the transformation directly using elemental fluorine, but unfortunately its use for the site specific fluorination of aliphatic compounds is rarely satisfactory due to its high reactivity which leads to unspecific multiple substitution, carbon-carbon bond cleavage and oxidation.

WO95/14646 discloses a method for the fluorination of certain 1,3-diketones and 1,3-ketoesters using elemental fluorine.

Surprisingly, we have now found that elemental fluorine can be used to convert N,N-disubstituted-1,3-ketoamides into the corresponding 2-fluoro-compounds in good yield. According to the present invention, there is provided a process for the preparation of an N,N-disubstituted-2-fluoro-1,3-ketoamide having the formula RCO.CFR'CONR$_2$" which comprises treating an N,N-disubstituted-1,3-ketoamide having the formula RCO.CHR'CONR$_2$" with elemental fluorine, wherein the groups R, R' and R" are independently selected from alkyl, aryl, substituted aryl, cycloalkyl, and substituted cycloalkyl and wherein the group R' may also be nitro or chlorine.

Preferably, the group R contains from 1 to 12 carbon atoms and the groups R' and R" contain from 1 to 8 carbon atoms. More preferably, the groups R, R' and R" contain from 1 to 6 carbon atoms.

Preferably, the fluorine is diluted with an inert gas such as nitrogen, helium or argon. The concentration of fluorine is preferably in the range 1–50 vol. %, more preferably from 2–25 vol. % and most preferably from 5–15 vol. %.

Preferably, the N,N-disubstituted-1,3-ketoamide is present in a solvent which is substantially inert to fluorine. Examples of such solvents are neutral substances such as acetonitryl and water, or acid substances such as formic acid. The solvent may be a mixture of these types of solvent.

Preferably, the concentration of N,N-disubstituted-1,3-ketoamide in the solvent is from 0.1 mol/l to 10 mol/l, although higher concentrations may be used.

Preferably, the reaction is carried out at a temperature in the range −60° C. to +150° C., more preferably from −20° C. to +50° C. and most preferably from −10° C. to +15° C.

The following Examples serve to illustrate the present invention. In these Examples, chemical shifts are measured in ppm from CFCl$_3$ or tetramethyl silane. Coupling constants are measured in Hertz.

EXAMPLE 1

Fluorination of N,N-diethylacetoacetoamide

Through a stirred solution of N,N-diethylacetoacetoamide (3.9 g. 0.025 m) in formic acid (50 ml) was bubbled fluorine (0.05 m), diluted with nitrogen to 10% fluorine, over 3.5 hours. The internal temperature was maintained in the range 4–8° C. When the reaction was complete, the vessel was purged with nitrogen and the solvent was removed under reduced pressure using a rotary evaporator to leave a pale orange viscous liquid. This liquid was distilled at reduced pressure using a short path distillation apparatus to give 2.2 g of a pale yellow liquid. Analysis of the distillate by gas chromatography indicated that all the starting material had reacted. Further purification was carried out by column chromatography (SiO$_2$/ethyl acetate) to give N,N-diethyl-2-fluoroacetoacetoamide (Found: C, 54.3; H, 8.1; N, 7.8. C$_8$H$_{14}$NO$_2$ requires C, 54.8; H, 8.0; N, 8.0.); m/z=175; δ$_F$-188.7 (dd, F$_{HF}$49.5, J$_{HH}$4.3); δ$_H$ 5.3 (d,J$_{HF}$49.9, 1H, —CHF—), 3.26 (m, 4H,NCH$_2$CH$_3$), 2.18 (d,J=4.0, 3H, CH$_3$COCHF), 1.08 (t, J=7.2, 3H, —CH$_2$CH$_3$), 1.00 (t, J=7.0, 3H, —CH$_2$CH$_3$); δ$_C$201.7 (d, $^2$J$_{CF}$24.0, CH$_3$COCHF—), 162.8 (d, $^2$J$_{CF}$20.2, CO.N<), 91.25 (d, $^1$J$_{CF}$ 194.9, CHF), 41.47 (s, CH$_2$CH$_3$), 40.41 (s, CH$_2$CH$_3$), 25.73 (s, CH$_3$CO) 13.90 (s, CH$_2$CH$_3$), 12.20 (s, CH$_2$CH$_3$).

Mass spectrometry indicated that minor components of the reaction product were difluorinated compounds.

EXAMPLE 2

Fluorination of N,N-diethylacetoacetoamide

Through a stirred solution of N,N-diethylacetoacetoamide (3.9 g. 0.025 m) in dry acetonitrile (50 ml) was bubbled fluorine (0.05 m), diluted with nitrogen to 10% fluorine, over 4.5 hours. The internal temperature was maintained in the range 4–8° C. When the reaction was complete, the vessel was purged with nitrogen and the solvent was removed under reduced pressure using a rotary evaporator to leave a pale orange viscous liquid. This liquid was distilled at reduced pressure using a short path distillation apparatus to give 2.75 g of a pale yellow liquid. Analysis of the distillate by gc/ms indicated that all the starting material had reacted, that the main reaction product was N,N-diethyl-2-fluoroacetoacetoamide and that minor components of the reaction mixture were di-, tri- and even a trace of tetrafluorinated material.

EXAMPLE 3

Fluorination of N,N-diethylacetoacetoamide

In a similar experiment to that outlined in Example 1, N,N-dimethylacetoacetoamide (4.6 g 70% aqueous solution, 0.025 m) was fluorinated to give N,N-dimethyl-2-fluoroacetoacetoamide, (Accurate mass measurement (EI); Found: 147.0696, C$_6$H$_{10}$FO$_2$N requires 147.0696.). δ$_F$-189.3 (d, J$_{HF}$49.7,); δ$_H$ 5.56 (d, J$_{HF}$49.8, 1H, —CHF—), 3.14 (s, 3H, NCH$_3$), 3.03 (s, 3H, NCH$_3$), 2.37 (d, J$_{HH}$=4.2, 3H CH$_3$CO); δ$_C$ 201.7 (d, $^2$J$_{CF}$ 24.0, CH$_3$COCHF—), 163.5 (d, $^2$J$_{CF}$ 20.4, CO.N<), 91.3 (d, $^1$J$_{CF}$ 195.2, CHF), 36.9 (s, CH$_3$), 35.9 (s, CH$_3$), 25.9 (s, CH$_3$CO).

What is claimed is:

1. A process for the preparation of an N,N-disubstituted-2-fluoro-1,3-ketoamide having the formula RCO.CFR'CONR$_2$" which consists essentially of treating an N,N-disubstituted-1,3-ketoamide having the formula RCO.CHR'CON$_2$" with elemental fluorine, wherein the groups R, R', and R" are independently selected from alkyl, aryl, substituted aryl, cycloalkyl, and substituted cycloalkyl and wherein the group R' may also be hydrogen, nitro or chlorine.

2. A process according to claim 1, wherein the fluorine is diluted with an inert gas.

3. A process according to claim 2, wherein the concentration of fluorine is in the range 1–50 vol. %.

4. A process according to claim 3, wherein the concentration of fluorine is from 2–25 vol. %.

5. A process according to claim 3, wherein the concentration of fluorine is from 5–15 vol. %.

6. A process according to claim 1, wherein the N,N-disubstituted-1,3-ketoamide is present in a solvent.

7. A process according to claim 6, wherein the solvent is a neutral substance.

8. A process according to claim 7, wherein the solvent is acetonitrile or water.

9. A process according to claim 6, wherein the solvent is an acid substance.

10. A process according to claim 9, wherein the solvent is formic acid.

11. A process according to claim 6, wherein the solvent is a mixture of acid and neutral solvents.

12. A process according to claim 6, wherein the concentration of N,N-disubstituted-1,3-ketoamide in the solvent is from 0.1 mol/l to 10 mol/l.

13. A process according to claim 6, wherein the reaction is carried out at a temperature in the range −60° C. to +150° C.

14. A process according to claim 13, wherein the reaction is carried out at a temperature in the range −20° C. to +50° C.

15. A process according to claim 13, wherein the reaction is carried out at a temperature in the range −10° C. to +15° C.

* * * * *